(12) United States Patent
Hoshino et al.

(10) Patent No.: US 6,569,634 B1
(45) Date of Patent: May 27, 2003

(54) METHOD FOR ASSAYING HUMAN THYMIDYLATE SYNTHASE AND ASSAY KIT

(75) Inventors: Nobuhiro Hoshino, Tokyo (JP); Takeshi Matsuya, Tokyo (JP); Masakazu Fukushima, Hanno (JP); Hiroyuki Okabe, Iruma (JP)

(73) Assignees: Taiho Pharmaceutical Co., Ltd., Tokyo (JP); Iatron Laboratories Inc., Tokyo (JP)

( * ) Notice: Subject to any disclaimer, the term of this patent is extended or adjusted under 35 U.S.C. 154(b) by 0 days.

(21) Appl. No.: 09/530,453

(22) PCT Filed: Aug. 31, 1999

(86) PCT No.: PCT/JP99/04708
§ 371 (c)(1),
(2), (4) Date: May 1, 2000

(87) PCT Pub. No.: WO00/13023
PCT Pub. Date: Mar. 9, 2000

(30) Foreign Application Priority Data

Sep. 1, 1998 (JP) .......................................... 10-247321

(51) Int. Cl.$^7$ .......................................... G01N 33/574
(52) U.S. Cl. .................................. 435/7.23; 530/389.1
(58) Field of Search ........................ 435/7.23; 530/389.1

(56) References Cited

U.S. PATENT DOCUMENTS 5,998,151 A * 12/1999 Johnston et al. ............. 435/7.1

FOREIGN PATENT DOCUMENTS

DE 31 15 115 A1 2/1982 .......... G01N/33/54
EP 0126173 A1 11/1984

OTHER PUBLICATIONS

Tolleson et al. Bioconjugate Chem. 2:327–332, 1991.*
Johnston et al. Biochemical Pharmacology, 45/12:2483–2486, Jun. 1993.*
Okabe et al. Oncology Reports 4:685–690, 1997.*
Weitz et al. International Journal of Oncology 2:275–278, 1993.*
Liddell et al., Antibody Technology, Bios Scientific Publishers, Oxford, UK, 1995.*
International Search Report.
Okabe et al., Jpn J Cancer & Chemotherapy, vol. 24, No. 6, (Apr., 1997) pp 705–712.
Yamachika et al., Cancer, "A New Prognostic Factor for Colorectal Carcinoma, Thymidylate Synthase, and Its Therapeutic Significance", 82,1 (Jan., 1998) pp. 70–77.
Men'eki Kagakuteki Duteihou, J. Clausen, 3$^{rd}$ Edition (1993), p. 182, including a copy of the cover page and imprint of the book, and an English translation of the relevant portion.
XP–002156191, Patrick G. Johnston, James C. Drake, Jane Trepel, and Carmen J. Allegra "Immunological Quantitation of Thymidylate Synthase Using the Monoclonal Antibody TS 106 in 50fluorouracil–sensitive and –resistant Human Cancer cells", Cancer Research, vol. 52, pp. 4306–4312, Aug. 15, 1992.
XP002926146, Patrick G. Johnston, Chi–Ming Liang, Sally Henry, Bruce A. Chabner, and Carmen J. Allegra "Production and Characterization of Monoclonal Antibodies That Localize Human Thymidylate Synthase in the Cytoplasm of Human Cells and Tissue", Cancer Research, vol. 51, 6668–6676, Dec. 15, 1991.
XP002926147, Malgorzata J. Jastreboff, Mary B. Todd, Harry L. Malech and Joseph R. Bertino "Isolation and Functional Effects of Monoclonal Antibodies Binding to Thymidylate Syntase", Biochemistry 1985, vol. 24, pp. 587–592, 1985.

* cited by examiner

*Primary Examiner*—Sheela Huff
(74) *Attorney, Agent, or Firm*—Sughrue Mion, PLLC

(57) ABSTRACT

This invention relates to a method for immunologically measuring human thymidylate synthase with an anti-human thymidylate synthase antibody, wherein as the antibody, at least an anti-human thymidylate synthase polyclonal antibody immobilized on an insoluble matrix is used; a method for evaluating sensitivity of cancer cells to a fluoropyrimidine antitumor drug from the results of the measurement by the measuring method; and a human thymidylate synthase measuring kit comprising an insoluble matrix with at least one anti-human thymidylate synthase polyclonal antibody immobilized thereon. By a simple immunological measuring method, human TS in a sample can be measured with high sensitivity.

8 Claims, 2 Drawing Sheets

METHOD FOR ASSAYING HUMAN THYMIDYLATE SYNTHASE AND ASSAY KIT

TECHNICAL FIELD

This invention relates to an immunological method for measuring human thymidylate synthase and also to a kit for the same.

BACKGROUND ART

Thymidylate synthase (EC2.1.1.45, hereinafter called "TS") is an enzyme that catalyzes a reaction in which thymidylic acid is formed from deoxyuridylic acid, plays a role to supply thymine which is a base specific to DNAs, and is one of principal rate-limiting enzymes for a DNA precursor supply pathway. Accordingly, its activity is known to become higher in normal or tumor tissues where cell growth is active.

On the other hand, fluoropyrimidine antitumor drugs such as 5-fluorourasil and 5-fluorodeoxyuridine act against TS as a target enzyme, and for example, 5-fluorodeoxyuridine changes into fluorodeoxyuridylic acid in vivo and inhibits TS. In particular, fluoropyrimidine antitumor drugs are known to show high administration effect and marked life prolongation effect for patients with a small amount of TS in tumor cells but to exhibit low administration effect for patients with TS in a large amount ["Gan to Kagaku Ryoho (Cancers and Chemotherapy)", 24(6), 705–712 (1997)]. The importance of TS is therefore high, for example, an advance measurement of the amount of TS in an excised tumor upon treatment of a tumor patient gives indications for the determination of a treatment method and for the selection of an antitumor drug.

As conventional TS measuring methods, methods which involve biochemical measurement of its enzyme activity are practiced primarily, including, for example, a method in which formation of dihydrofolic acid as a reaction product is measured by an absorbance at a specific wavelength and a method in which the amount of radiolabeled fluorodeoxyuridylic acid (FdUMP) (for example, [3H]FdUMP) which binds to TS is measured.

On the other hand, immunological measuring methods making use of anti-TS antibodies have also been reported. Known methods include, for example, a method in which TS is measured by using anti-TS monoclonal antibodies M-TS-4 and M-TS-9 [Malgorzata M. Jastreboff et al., Biochemistry, 1985(24), 587–592]; and a method in which TS is detected using anti-TS monoclonal antibodies TA 102, TS 105, TS 106, TS 109, TS 110, TS 11A and TS 11B [Japanese Language Laid-Open Publication (PCT) No. HEI 6-507314]. Also known are a blotting method in which various homogenized tumor cells are subjected to electrophoresis and subsequent to transferring, an anti-TS-IgG antibody and a labeled anti-IgG are used as a primary antibody and a secondary antibody, respectively ["Gan to Kagaku Ryoho (Cancers and Chemotherapy)", 24(6), 705–712 (1997)]; a method in which wells are coated with a standard TS antigen and a TS-containing test sample and an anti-TS antibody are then added to cause competition; and a method in which wells are coated with a TS-containing test sample, an anti-TS antibody is added and bound, and labeled anti-mouse IgG is then reacted.

However, the above-described methods which biochemically measure the enzyme activity of TS are accompanied by many problems in that inter alia the sensitivity is insufficient to measure enzyme activity of low level, use of fresh samples is needed, test samples must be carefully handled to avoid enzymatic degradation, test samples are required in large amounts, and special techniques and facilities are needed if a radioactive substance is handled.

Further, the conventional immunological measurement methods are not considered to be sufficient in the irksomeness of procedures and the accuracy of measurements. Described specifically, for example, the method in which a detection is performed by blotting subsequent to electrophoresis is accompanied by a problem in that it is poor in quantitativeness although its procedures are very complex, the method in which a test sample and an antibody are competitively reacted on antigen-coated wells involves a problem in that it has poor measurement sensitivity, and even the method in which a diluted solution of a test sample is coated on wells as it is involves a problem in that TS cannot necessarily be coated in its entirety, resulting in poor reliability. It is therefore the current situation that there is an outstanding demand for a simple and high-accuracy method for the measurement of TS.

DISCLOSURE OF THE INVENTION

With the foregoing circumstances in view, the present inventors have proceeded with various investigations. As a result, it has been found that use of an anti-human TS polyclonal antibody immobilized on an insoluble carrier is very effective for specifically and efficiently capturing a trace amount of human TS from a test sample which contains a great number of components (impurities), leading to the completion of the present invention.

The present invention therefore provides a method for immunologically measuring human thymidylate synthase with an anti-human TS antibody, wherein as the antibody, at least an anti-human TS polyclonal antibody immobilized on an insoluble carrier is used.

The present invention also provides a method for evaluating sensitivity of cancer cells to a fluoropyrimidine antitumor drug, which comprises measuring an amount of human TS contained in a sample of the cancer cells by the above-described method and determining the sensitivity from results of the measurement.

The present invention also provides a human TS measuring kit comprising an insoluble carrier with at least one anti-human TS polyclonal antibody immobilized thereon.

BEST MODES FOR CARRYING OUT THE INVENTION

Figure 1:
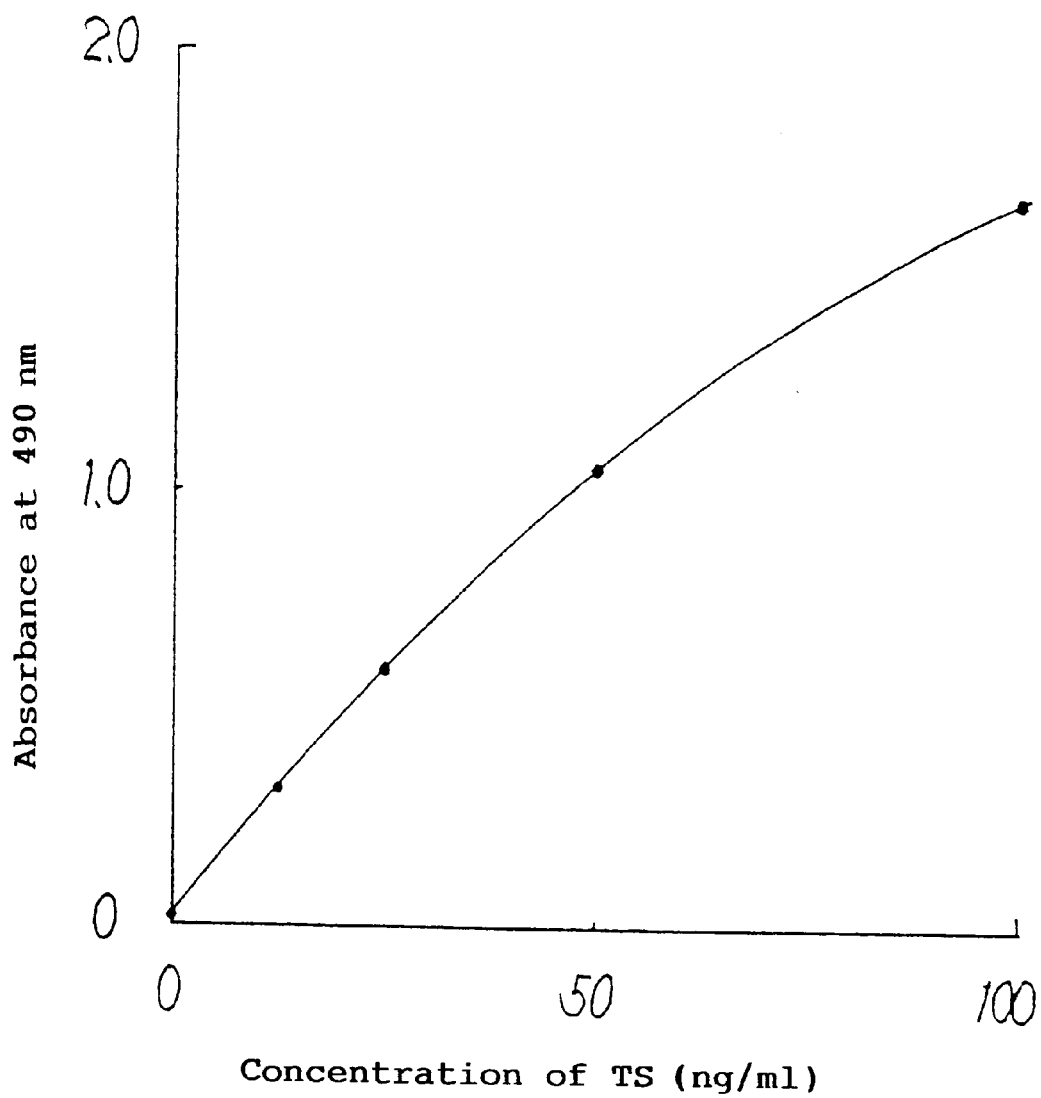
FIG. 1 is a graph showing a standard curve of TS concentration versus absorbance in an anti-human TS polyclonal antibody immobilized plate-enzyme-labeled anti-human TS polyclonal antibody system.

To obtain the anti-human TS polyclonal antibody for use in the present invention, human TS is used as an immunogen. As human TS, native human TS available from the living body by extraction and purification (hereinafter called "nhTS") can be used or, where it is desired to obtain human TS more easily in a large amount, recombinant human TS (hereinafter called "rhTS") can also be used. rhTS is readily available, and has merits in that its use makes it possible to obtain an antibody with uniform reactivity and also facilitates constitution of a system, measuring performance of which always remains constant, in a measuring kit. rhTS is therefore preferred.

nhTS can be obtained, for example, as will be described hereinafter. nhTS can be obtained with high purity by loading incubated cells of a TS-expressing human tissue or a tumor strain, which has been derived from a human tumor or a homogenate of a tumor subcutaneously transplanted in a nude mouse or nude rat, onto a column while using ethyl 10-formyl-5,8-dideazafolate as a ligand and then conducting elution with a dUMP-containing buffer.

As an alternative, rhTS can also be obtained, for example, as will be described hereinafter. Firstly, a plasmid, which can derive a glutathion S-transferase (GST)-TS fused protein by isopropyl-1-thio-β-D-galactoside (IPTG), is prepared by determining the DNA sequence of human TS and then inserting a translation region in a plasmid designed to produce the GST-TS fused protein. An *Escherichia coli* strain which has been transfected with the plasmid is mass-incubated in the presence of IPTG, and the incubation medium is loaded onto a glutathion-agarose column. The thus-adsorbed GST-TS fused protein is eluted with a suitable buffer, and is then heated in the presence of thrombin and calcium chloride to cleave human TS and GST from each other. The resulting mixture is loaded further onto a GST-agarose column, whereby rhTS of high purity can be obtained.

The anti-human TS polyclonal antibody for use in the present invention can be obtained in a manner known per se in the art by administering such human TS (for example rhTS) to a suitable mammal such as a mouse, rat, rabbit or sheep.

Owing to the use of the anti-human TS polyclonal antibody in a form immobilized on an insoluble carrier, the present invention has made improvements to the problems of the conventional immunological measuring methods, that is, the irksomeness of procedures and the low accuracy of measurement, and can achieve extremely high sensitivity.

The method of the present invention for the measurement of human TS can be applied to any measuring system insofar as it uses an anti-human TS polyclonal antibody immobilized on insoluble carrier or, if necessary, the antibody and a different kind of anti-human TS antibody in combination. Specifically, the measuring method of the present invention can be suitably applied, for example, to latex agglutination, immunochromatography, the sandwich method, competitive radioimmunoassay, enzyme immunoassay and the like, especially to the sandwich method and latex agglutination.

To apply the method of the present invention to latex agglutination, for example, latex particles are coated with the anti-human TS polyclonal antibody, the antibody-coated latex particles so sensitized are reacted with a test sample containing human TS, and a change in absorbance due to resulting agglutination is then measured, whereby human TS can be quantitated.

To apply the method of the present invention to the competitive assay, for example, an anti-human TS polyclonal antibody immobilized matrix, a test sample containing human TS, and labeled human TS are competitively reacted, and the label activity of the labeled human TS bound to the matrix is then measured, whereby human TS can be quantitated.

To apply the method of the present invention to the sandwich method, for example, an anti-human TS polyclonal antibody immobilized matrix and a test sample containing human TS are reacted to form a complex, the reaction medium is removed, a labeled anti-human TS antibody is next reacted to form a sandwich-like reaction product of the anti-human TS polyclonal antibody immobilized matrix and the labeled anti-human TS antibody, any excess portion of the labeled antibody is removed by washing, and the quantity of the label immobilized on the matrix is then measured, whereby human TS can be quantitated.

Specific examples of materials employed in the sandwich method can include, as a matrix, a glass tube or plate or glass wells or beads, a plastic tube or plate or plastic wells or beads, or ferrite particles. The anti-human TS polyclonal antibody is caused to bind to the matrix by known physical adsorption or chemical bonding, and is used as an antibody immobilized matrix.

For labeling, an enzyme, a radioactive isotope, a fluorescent substance or the like can be used. Of these, an enzyme is preferred. As this enzyme, those having excellent stability and permitting easy measurements of enzyme activities can be suitably used, such as peroxidase, alkaline phosphatase, glucose oxidase and galactosidase. Examples of a method for causing such an enzyme to bind to the antibody can include binding reactions between amino groups of enzyme and antibody with a glutaraldehyde and binding reactions making use of a crosslinking agent containing a succinimido group, a maleimido group or the like. A method in which the sugar chain of a peroxidase is oxidized with periodic acid and is allowed to bind to an amino group of an antibody is also preferred for its good yield and simple procedures.

As a substrate for the measurement of enzyme activity, one specific to the enzyme is used. Human TS can be quantitated by causing color dye, fluorescence, light emission or the like to occur and then detecting its signal by a measuring instrument. When a peroxidase is used as an enzyme, for example, use of hydrogen peroxide and ortho-phenylenediamine in combination causes a color dye producing reaction to occur in proportion to the amount of the enzyme, and use of hydrogen peroxide and luminol in combination causes a light emitting reaction to occur. A signal corresponding to the amount of the enzyme can be obtained by performing a measurement with a spectrophotometer in the case of the color dye producing reaction or with a luminometer in the case of the light emitting reaction.

To apply the method of the present invention to immunochromatography, a known material capable of developing a liquid, such as paper or thin cellulose film, is used as an insoluble matrix. By developing a liquid sample containing human TS, the anti-human TS polyclonal antibody is immobilized at a detecting position. For the immobilization, known methods can be used, with a method relying upon chemical bonds being particularly preferred. A labeled anti-human TS antibody is contained in a position onto which the liquid sample is dropped or to an intermediate point on a route along which the dropped liquid sample is developed. Since irreversible adsorption of the labeled anti-human TS antibody on the insoluble matrix is not preferred, it is preferred to solidify the labeled anti-human TS antibody on a thin film by using a high molecular substance (polyvinylpyrrolidone, polyethylene glycol, or a high molecular saccharide such as dextran). Usable examples of the labeling material can include, in addition to the above-described enzymes, metal colloids such as gold colloid and platinum; latex particles colored with dyestuff (so-called color latexes); various fluorescent reagents such as fluorescein and europium chelate; and luminescent reagents such as acridinium derivatives. Metal colloids or color latexes are preferably used as they do not require any additional sensitizing reaction and permit visual observations.

Into the human TS in the sample dropped onto the insoluble matrix, the labeled anti-TS antibody is first progressively bound and developed. The labeled anti-TS antibody is then captured and allowed to concentrate at the position of the immobilized anti-human TS polyclonal antibody, and a degree of coloration or the like originated from the label at the position is detected visually or by use of an optical apparatus, whereby the human TS can be measured.

When in addition to the immobilized anti-human TS polyclonal antibody, a labeled antibody different in kind from the first-mentioned antibody is used in combination, illustrative of such an antibody are anti-human TS polyclonal antibodies and monoclonal antibodies.

When an anti-human TS monoclonal antibody is used, the anti-human TS monoclonal antibody can be obtained by incubating a hybridoma (for example, mouse hybridoma), which can produce the monoclonal antibody, for example, in a suitable medium or within the peritoneal cavity of a mammal (for example, mouse).

In general, this hybridoma can be prepared, for example, by subjecting spleen cells of an rhTS- or nhTS-immunized mammal or bird (for example, mouse) and myeloma cells of a mammal (for example, mouse) to cell fusion in accordance with the method originally outlined by Kohler and Milstein [see Nature, 256, 495 (1975)]. An illustrative medium suitably usable for the incubation of the hybridoma is a media which contains bovine fetal serum, L-glutamine, L-pyruvic acid, and antibiotics (penicillin G and streptomycin) in Dulbeccos modified Eagle's minimum essential medium. The incubation of the hybridoma is conducted, for example, at 5% $CO_2$ concentration and 37° C. for 3 days when it is performed in an incubation medium or, for example, for 14 days when it is performed within the peritoneal cavity of a mouse. From the incubation medium or mammalian ascitic fluid obtained as described above, the anti-human TS monoclonal antibody can be separated and purified by a method commonly employed for the isolation and/or purification of proteins. Examples of such a method can include salting-out with ammonium sulfate, ion-exchange column chromatography making use of an ion-exchange cellulose, molecular sieve column chromatography making use of a molecular sieve gel, affinity column chromatography making use of polysaccharide complexed with protein A, dialysis, and lyophilization.

Illustrative of the anti-human TS monoclonal antibody available as described above are those produced by mouse hybridomas RTSMA1 (FERM BP-6404), RTSMA2 (FERM BP-6402), NTSMA1 (FERM BP-6401) and NTSMA2 (FERM P-6403) as will be described subsequently in Examples. These hybridomas have been deposited under the Budapest Treaty in National Institute of Bioscience and Human-Technology, Agency of Industrial Science and Technology, Ministry of International Trade and Industry (address: 1–3, Higashi 1-chome, Tsukuba-shi, Ibaraki-ken 305-0046, JAPAN) (date of original deposit: Jun. 30, 1998). The use of an anti-human TS polyclonal antibody immobilized on an insoluble matrix in combination with such a monoclonal antibody or polyclonal antibody in the present invention makes it possible to measure human TS with good accuracy.

By using an anti-human TS polyclonal antibody immobilized matrix and also by selecting a labeled antibody, a substrate and a measuring instrument in accordance with each assay system, the detection of human TS becomes feasible. Further, a human TS measuring kit which is useful for the measuring method of this invention can be constituted by using an insoluble matrix with at least one kind of anti-human TS polyclonal antibody immobilized thereon and also by suitably choosing other elements in accordance with each assay system.

EXAMPLES

The following examples are presented to illustrate the present invention in further detail, but it is to be understood that the present invention is not limited thereto.

Referential Example 1
A. Preparation of rhTS

An *Escherichia coli* strain NM522, in which a plasmid prepared with restriction endonuclease recognition sites MunI to HindIII of human TS cDNA incorporated therein to express a fused protein of glutathione S-transferase (GST) and human TS had been introduced, was incubated overnight at 37° C. under shaking in LB medium (200 mL) (product of Wako Pure Chemical Industries, Ltd.) in the presence of ampicillin (50 µg/mL). The incubation medium was poured in 100 mL aliquots into two Erlenmeyer flasks which contained ampicillin-containing LB medium (1 liter/flask). They were incubated at 25° C. for 3 hours under shaking, to which 0.6 mL aliquots of isopropyl-1-thio-β-D-galactoside (IPTG, 40 mg/mL) were added respectively, followed by further incubation at 25° C. for 20 hours. Cells were collected by centrifugation and were then suspended in a disrupting buffer (100 mL; 50 mM Tris, pH 7.5, 25% sucrose). "10% Nonidet P-40" (5 mL; surfactant, product of NACALAI TESQUE INC.) and 1 M magnesium chloride (0.5 mL) were added. The cells were disrupted by a sonicator, followed by centrifugation at 10,000 rpm for 15 minutes. The supernatant was caused to pass (20 mL/hr) through a column packed with glutathione (GSH)-agarose (14 mL; product of Sigma Chemical Co.). After the column was washed with a washing-buffer (100 mL; 20 mM Tris, pH 7.5, 2 mM magnesium chloride, 1 mM DTT), the column was eluted with an eluting-buffer (50 mL; 50 mM Tris, pH 9.6, 5 mM GSH) such that the eluate was received in 3-mL aliquots in tubes. By confirming protein fractions in accordance with the Bradford's method, peak fractions (9 mL; protein concentration: 7 mg/mL) were obtained. They were immediately dialyzed against a washing-buffer described above (1 liter) to lower their pH back to 7.5, and thrombin (600 units) was added. The reaction mixture was treated at 37° C. for 2 hours in the presence of 1 mM calcium chloride, whereby the GST-TS fused protein was cleaved at bound sites. The resulting mixture of GST and TS was again caused to pass through a GSH-agarose column (20 mL/hour), the column was eluted with a washing-buffer, and protein fractions were confirmed by the Bradford's method, whereby an rhTS solution (9 mL) was obtained. 0.2, 0.4, 0.6, 0.8 and 1.0 mg/mL BSA solutions (100 µL) were added to 5-mL aliquots of the Bradford's solution, respectively, and their absorbances at 595 nm were measured to prepare a standard curve. An rhTS solution (100 µL), which had been diluted fivefold in distilled water, was added to the Bradford's solution (5 mL) and the absorbance at 595 nm was measured. As a result, the protein concentration of the rhTS solution was found to be 3.5 mg/mL.

B. Preparation of nhTS

Purification of nhTS was conducted based on the method proposed by Rode et al. [Rode et al., Biochemical Pharmacology, 29, 723 (1980)]. A human lung cancer strain Lu-99, which had been subcutaneously transplanted to dorsal regions of 50 male BALB/c-nu/nu mice, was removed to obtain tumors (50 g). Those tumors were added with 10 mM phosphate buffer (100 mL; pH 7.5, 100 mM potassium chloride, 10 mM 2-mercaptoethanol) and were then homogenized. The homogenate was centrifuged at 4° C. and 10,000 rpm for 1 hour, and from the supernatant, a precipitate was obtained with ammonium sulfate at 30–70% saturation. The precipitate was dissolved in 10 mM phosphate buffer (pH 7.5, 0.1% Triton X-100, 10 mM 2-mercaptoethanol, 20 $\mu$M dUMP). The resulting solution was loaded onto an affinity column while using ethyl 10-formyl-5,8-dideazafolate as a ligand. After the column was washed with 200 mM phosphate buffer (pH 7.5, 0.1% Triton X-100, 10 mM 2-mercaptoethanol, 20 $\mu$M dUMP), nhTS proteins were eluted with 200 mM phosphate buffer (pH 7.5, 0.1% Triton X-100, 10 mM 2-mercaptoethanol, 20 $\mu$M dUMP) and collected (4 mL). 0.2, 0.4, 0.6, 0.8 and 1.0 mg/mL BSA solutions (100 $\mu$L) were added to 5-mL aliquots of the Bradford's solution, respectively, and their absorbances at 595 nm were measured to prepare a standard curve. An nhTS solution (100 $\mu$L) was added to the Bradford's solution (5 mL) and the absorbance at 595 nm was measured. As a result, the protein concentration of the nhTS solution was found to be 0.3 mg/mL.

Referential Example 2

Procedures for Preparing a Polyclonal Antibody by Using rhTS as an Immunogen

To a rabbit (New Zealand White, female, 12 weeks old), the rhTS obtained in Referential Example 1A was subcutaneously administered at a dose of 100 $\mu$g/rabbit at her dorsal region. The rhTS was used in a form emulsified beforehand in Freund's complete adjuvant. To the rabbit, the rhTS in a form emulsified beforehand in Freund's incomplete adjuvant was subcutaneously injected at a dose of 100 $\mu$g/rabbit four times successively at intervals of 14 days to her dorsal region. After seven days from the last immunization, a blood sample was collected from the rabbit and serum was then obtained by centrifugation. The serum was then caused to pass through a "Protein G Sepharose 4FF" column (product of Pharmacia AB). After the column was washed with a washing-buffer (20 mM sodium phosphate, pH 7.0), the antibody was eluted with an eluting-buffer (0.1 M glycine, pH 2.7) and was immediately dialyzed against the washing-buffer described above, whereby the antibody was purified as IgG. Further, a sample of the IgG fraction was loaded onto an rhTS-bound Sepharose 4B column. After the column was washed with a washing-buffer (20 mM sodium phosphate, pH 7.0), the antibody was eluted with the eluting-buffer (0.1 M glycine, pH 2.7) and was immediately dialyzed against a washing-buffer.

Referential Example 3

Preparation of a Monoclonal Antibody by Using rhTS as an Immunogen

To a female BALB/c mouse (8 weeks old), the rhTS obtained in Referential Example 1A was intraperitoneally injected at a dose of 20 $\mu$g/mouse. The TS protein was used in a form emulsified beforehand in Freund's complete adjuvant. To the mouse, the rhTS in a form emulsified beforehand in Freund's incomplete adjuvant was additionally and intraperitoneally injected at a dose of 20 $\mu$g/mouse four times successively at intervals of 14 days. Three days before fusion, the rhTS (100 $\mu$g) in phosphate-buffered physiological saline (0.5 mL) was injected through a caudal vein. Using spleen cells ($1 \times 10^3$) from the immunized mouse, P3×63 Ag8 variant 653 myeloma cells ($2 \times 10^7$) and as a fusing reagent, "50% (V/V) polyethylene glycol 4000" (product of Merck & Co., Inc.), those cells were caused to fuse together in accordance with the fusing method proposed by Galfre and Milstein [Galfre et al., Nature 266, 550 (1977)].

After the fusion, cells were suspended in HAT medium (RPMI1640 medium containing $1 \times 10^{-4}$ M hypoxanthine, $4 \times 10^{-7}$ M aminopterin and $1.6 \times 10^{-5}$ M thymidine), which contained 10% bovine fetal serum, to give a cell concentration of $1 \times 10^6$ cells/mL. The resultant suspension was dispensed in 200 $\mu$L aliquot per well onto a 96-well microplate.

Fused cells were incubated in a $CO_2$ incubator (5% $CO_2$, 37° C.), during which replacements of the medium were conducted using HAT medium containing 10% bovine fetal serum so that the fused cells were allowed to proliferate. A hybridoma formed of the spleen cells and the myeloma cells were screened, and was then conditioned in HT medium (RPMI1640 medium containing $1 \times 10^{-4}$ M hypoxanthine and $1.6 \times 10^{-5}$ M thymidine) which contained 10% bovine fetal serum.

The antibody in the incubation supernatant of the hybridoma was detected in accordance with ELISA by using an rhTS-sensitized microplate. With respect to each well which was found to be positive, cloning was repeated twice in accordance with the limiting dilution analysis by using HT medium which containing 10% bovine fetal serum and 5% Bleiclone (product of Dainippon Pharmaceutical Co., Ltd.). Two kinds of clones which had reactivity to the rhTS were hence chosen, and were named "RTSMA1" (FERM BP-6404) and "RTSMA2" (FERM BP-6402).

A monoclonal antibody produced by each of the clones was obtained as will be described next. Pristane (0.5 mL; product of Dainippon Pharmaceutical Co., Ltd.) was intraperitoneally injected to a nude mouse. Seven days later, pristane (0.5 mL) was intraperitoneally administered further, and the hybridoma ($1 \times 10^7$ cells) was transplanted to the peritoneal cavity and was allowed to proliferate. After 2 to 3 weeks, ascitic fluid was obtained. The ascitic fluid was caused to pass through a "Protein G Sepharose 4FF" column (product of Pharmacia AB). After the column was washed with a washing-buffer (20 mM sodium phosphate, pH 7.0), the antibody was eluted with the eluent (0.1 M glycine, pH 2.7) and was immediately dialyzed against a washing-buffer.

Referential Example 4

Preparation of a Monoclonal Antibody by Using nhTS as an Immunogen

In a similar manner as in Referential Example 3 except that as an immunogen, the nhTS obtained in Referential Example B1 was used in place of the rhTS, two kinds of clones having high reactivity to the nhTS were chosen, and were named "NTSMA1" (FERM BP-6401) and "NTSMA2" (FERM BP-6403). From these hybridomas, monoclonal antibodies were then obtained in a similar manner as in Referential Example 3.

Referential Example 5

Preparation of Measuring Antibodies (1) Digestion of Anti-TS Rabbit-specific Antibody with Pepsin The rabbit-specific antibody IgG fractions, which were obtained above in Referential Example 2, were dialyzed against 50 mM acetate buffer (pH 4.5). The dialyzate was added with pepsin in an amount of 2.5% based on the amount of IgG, and a digestive reaction was conducted for 16 hours in an incubator controlled at 37° C. After that, the digestive reaction was terminated by raising the pH to 8 with Tris solution, and by gel filtration making use of a "Sephacryl S-200" column, fractions of an antibody F(ab')$_2$ the molecular weight of which was 100,000 were pooled.

(2) Preparation of Antibody-immobilized Matrix

The fractions of antibody F(ab')$_2$, which had been obtained as described above, were adjusted to 2 μg/mL with 20 mM PBS (pH 7.0), and were then dispensed in 0.1 mL aliquots onto a 96-well ELISA plate. The plate was sealed and was then subjected to coating for 2 hours in an incubator controlled at 37° C., whereby an antibody-immobilized matrix was obtained. Upon use, the coated plate was washed twice with saline (wash) which contained 0.05% Tween 20, and was then employed in a reaction.

(3) Preparation of Peroxidase-labeled Antibody

Horseraddish peroxidase (2 mg; product of Toyobo Co., Ltd.) was dissolved in distilled water (0.5 mL), and subsequent addition of 0.2 M sodium metaperiodate (0.1 mL), a reaction was conducted at room temperature for 20 minutes under shaking. The reaction mixture was loaded onto a "Sephadex G-25" column [1.5 cm in diameter×12 cm, equilibrated with 1 mM acetate buffer (pH 4.2)], and brown enzyme fractions eluted with the buffer were pooled. Halves (1 mg) of the pooled enzyme were added to the polyclonal antibody IgG fraction (2 mg) and the monoclonal antibody IgG fraction (2 mg) (in 50 mM carbonate buffer (pH 9.5, 1 mL), respectively. Further, 0.1 mL aliquots of 1 M carbonate buffer were added, and reactions were conducted at room temperature for 2 hours under shaking. 0.1 mL aliquots of 4 mg/mL sodium borohydride were added and the resulting mixtures were allowed to stand at 4° C. for 1 hour, whereby the reactions were terminated. The reaction mixtures were then separately dialyzed against saline. The inner dialyzates were separately loaded onto "Sephacryl S-200" columns (2.5 cm in diameter×70 cm, equilibrated with physiological saline), and fractionated initial peaks were pooled as enzyme-labeled antibodies, respectively.

Test 1

Comparison of Antibody Combinations

A comparison was made in measurement sensitivity by combining the anti-human TS monoclonal antibody, which was obtained from the hybridoma "RTSMA1" (FERM BP6404) in Referential Example 3, with the anti-human TS polyclonal antibody prepared in Referential Example 5(1).

The monoclonal antibody IgG (RTSMA1) and the polyclonal antibody IgG, both of which had been adjusted to 2 μg/mL with 50 mM carbonate buffer (pH 9.5), were dispensed in 0.1 mL aliquots onto 96-well ELISA plates, respectively. The plates were sealed and were then subjected to coating for 2 hours in an incubator controlled at 37° C., whereby two kinds of antibody-immobilized matrixs were obtained. After those matrixs were washed twice with a wash, serial dilutions (0.1 mL) of purified rhTS, said dilutions having been prepared with 20 mM PBS containing 0.05% Tween 20 (diluent), were dispensed onto the antibody-immobilized plates, and the plates were statically allowed to react at 37° C. for 1 hour. After the plates were washed twice with a wash, enzyme-labeled antibodies (0.1 mL), which had been prepared from monoclonal antibody and polyclonal antibody obtained from the hybridoma "NTSMA1" (FERM BP-6401) obtained in Reference Example 4, were dispensed into the wells and were then statically allowed to react at 37° C. for 1 hour. After the wells were washed four times with a wash, 0.1 mL aliquots of 0.1 M acetate buffer (pH 5.5, color-producing solution) which contained 3 mg/mL orthophenylenediamine and 0.75 mM hydrogen peroxide were added, and enzyme reactions were allowed to proceed at room temperature for 30 minutes in a dark place. Finally, 0.1 mL aliquots of 1 M sulfuric acid were added to terminate the reactions, and measurements were conducted with the measuring wavelength of an ELISA plate reader set at 490 nm.

The results are presented in Table 1.

TABLE 1

| | Absorbance (490 nm) | | | |
|---|---|---|---|---|
| Concentration of rhTS (ng/mL) | Immobilized monoclonal antibody[1] & Labeled monoclonal antibody[2] | Immobilized monoclonal antibody[1] & Labeled polyclonal antibody | Immobilized polyclonal antibody & Labeled monoclonal antibody[2] | Immobilized polyclonal antibody & Labeled polyclonal antibody |
| 0 | 0.189 | 0.230 | 0.255 | 0.244 |
| 1 | 0.192 | 0.227 | 0.271 | 0.282 |
| 10 | 0.176 | 0.232 | 0.473 | 0.478 |
| 100 | 0.242 | 0.629 | 0.985 | 1.923 |
| 1000 | 0.928 | >3.0 | >3.0 | >3.0 |

[1]RTSMA1
[2]NTSMA1

As is apparent from Table 1, use of an immobilized monoclonal antibody plate has a poor response to rhTS of a low concentration and cannot provide any high-sensitivity measuring method, while use of an immobilized polyclonal antibody can bring about high sensitivity irrespective of the kind of a labeled antibody and can measure a trace amount of human TS.

Example 1

Measurement of Human TS (1) Measurement of a Standard and Human TS in a Sample

The protein amount of the purified rhTS obtained in Referential Example 1A was quantitated, and its value was recorded as a nominal value of the standard. The standard was diluted in 20 mM PBS (diluting solution) which contained 0.05% Tween 20, and the standard so diluted was provided for measurement. As a sample, a centrifugal supernatant of a cancer tissue homogenate was diluted tenfold in the diluting solution, and the thus-diluted supernant was provided for measurement. 0.1 mL aliquots of the standard or sample were dispensed onto an anti-human TS polyclonal antibody immobilized plate and were statically allowed to react at 37° C. for 1 hour. After the wells were washed twice with a wash, 0.1 mL aliquots of the enzyme-labeled antihuman TS polyclonal antibody which had been adjusted to an antibody amount of 1 μg/mL with the diluting solution were dispensed into the individual wells, and were statically allowed to react at 37° C. for 1 hour. After the wells were washed four times with a wash, 0.1 mL aliquots of 0.1 M acetate buffer (pH 5.5; color-developing solution) which contained 3 mg/mL orthophenylenediamine and 0.75 mM hydrogen peroxide were added, and an enzyme reaction was allowed to proceed at room temperature for 30 minutes in a dark place. Finally, 0.1 mL aliquots of 1 M sulfuric acid were added to terminate the reaction, and measurements were conducted with the measuring wavelength of an ELISA plate reader set at 490 nm.

(2) Preparation of a Standard Curve

A graph was prepared by plotting standard TS concentrations along the abscissa and the absorbances, which had been obtained above in the measurement (1), along the ordinate. As is shown in FIG. 1, a standard curve was obtained with the absorbance increasing with the concentration of the standard.

(3) Correlation with a Substrate Binding Method

A substrate binding method making use of tritium-labeled FdUMP was conducted based on the method proposed by Spears et al. [Spears et al., Cancer Research, 42, 450 (1982)]. A tumor tissue was added with three times its weight of a homogenizing buffer (200 mM Tris, pH 7.4, 20 mM 2-mercaptoethanol, 15 mM cytidine 5'-monophosphate, 100 mM sodium fluoride). Subsequent to homogenization, the mixture was centrifuged at 105,000×g for 1 hour to prepare a homogenate. The homogenate (50 μL) was added with buffer A (50 μL; 600 mM ammonium hydrogencarbonate, pH 8.0, 100 mM 2-mercaptoethanol, 100 mM sodium fluoride, 15 mM cytidine 5'-monophosphate), buffer B (25 μL; potassium phosphate, pH 7.4, 20 mM 2-mercaptoethanol, 15 mM cytidine 5'-monophosphate, 100 mM sodium fluoride, 2% BSA, 2 mM tetrahydrofolic acid, 16 mM sodium ascorbate, 9 mM formaldehyde), and 2 μCi/mL [$^3$H]FdUMP (50 μL). The resulting mixture was incubated at 30° C. for 20 minutes, and the radioactivity of an acid-insoluble fraction was measured. Assuming that TS and [$^3$H]FdUMP were bound with each other at 1:1, the amount of TS was calculated from the specific activity of [$^3$H]FdUMP.

Figure 2:
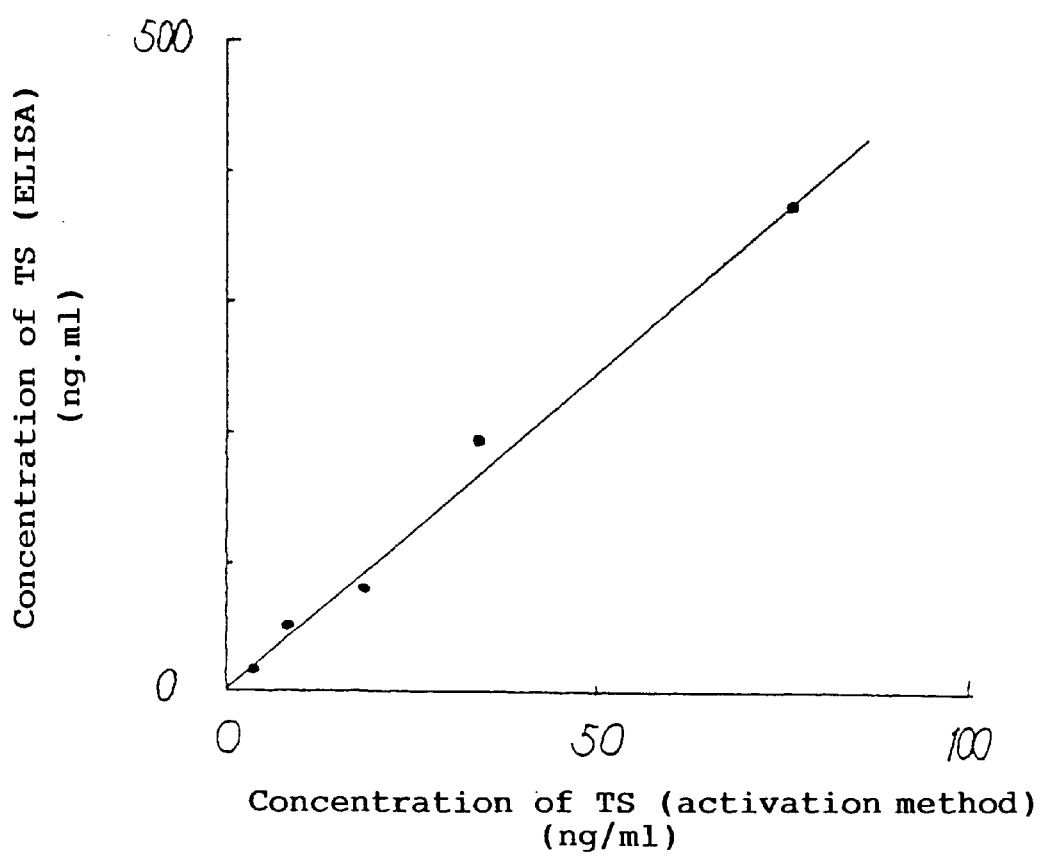
FIG. 2 is a graph illustrating a correlation between the substrate binding method (activation method) and the measuring method according to the present invention.

The amounts of human TS in the samples as obtained by the substrate binding method described above under (3) were plotted along the abscissa, while the values of concentrations converted from the absorbances of the samples, which were obtained by ELISA in the above measurement (1), by using the standard curve were plotted along the ordinate. As is shown in FIG. 2, a good correlation was observed.

Capability of Exploitation in Industry

As has been described above, the present invention has made it possible to measure human TS in a sample with high sensitivity by a simple immunological measuring method owing to the use of an anti-human TS polyclonal antibody immobilized on an insoluble matrix. Quantitation of human TS in a sample (for example, a stomach tissue extract) by the measuring method of the present invention permits not only determination of the presence or absence of a cancer, confirmation of therapeutic effect, and the like but also provision of an indication as to which treatment method should be chosen and whether or not administration of an antitumor drug is permissible.

What is claimed is:

1. A method for immunologically measuring human thymidylate synthase, which method comprises contacting a sample to be analyzed with at least an anti-human thymidylate synthase antibody F(ab')$_2$ fragment immobilized on an insoluble matrix.

2. The method according to claim 1, wherein said anti-human thymidylate synthase antibody F(ab')$_2$ fragment is an anti-human thymidylate polyclonal antibody F(ab')$_2$ fragment immobilized on an insoluble matrix and wherein said insoluble matrix on which an anti-human thymidylate synthase antibody F(ab')$_2$ fragment is immobilized is additionally contacted with a labeled anti-human thymidylate synthase antibody.

3. The method according to claim 2, wherein said anti-human thymidylate synthase antibody F(ab')$_2$ fragment is obtained using a recombinant human thymidylate synthase as an immunogen.

4. The method according to claim 1, wherein said anti-human thymidylate synthase antibody F(ab')$_2$ fragment is obtained using a recombinant human thymidylate synthase as an immunogen.

5. A method for evaluating sensitivity of cancer cells to a fluoropyrimidine antitumor drug, which method comprises measuring an amount of human thymidylate synthase contained in a sample of said cancer cells by the method claimed in any one of claims 1–4 and determining said sensitivity from results of said measurement.

6. The method according to claim 1, in which said method for measuring human thymidylate synthase is a measuring system selected from the group consisting of latex agglutination, immunochromatography, radioimmunoassay, and enzyme immunoassay.

7. The method according to claim 1, in which said method for measuring human thymidylate synthase is a sandwich method.

8. A human thymidylate synthase measuring kit comprising an insoluble matrix with at least one anti-human thymidylate synthase polyclonal antibody F(ab')$_2$ fragment immobilized thereon.

* * * * *